United States Patent [19]

Baumann et al.

[11] 4,349,565
[45] Sep. 14, 1982

[54] CYCLOBUTANEDICARBOXISOIMIDES AND USE THEREOF AS FUNGICIDES

[75] Inventors: Marcus Baumann, Basel; Niklaus Bühler, Rheinfelden; Daniel Bellus, Riehen, all of Switzerland

[73] Assignee: Ciba-Geigy Corporation, Ardsley, N.Y.

[21] Appl. No.: 251,835

[22] Filed: Apr. 8, 1981

[30] Foreign Application Priority Data

Apr. 14, 1980 [CH] Switzerland ............... 2858/80

[51] Int. Cl.³ .................. A61K 31/365; C07D 307/93
[52] U.S. Cl. ..................................... 424/279; 549/303
[58] Field of Search ............... 260/343.3 R; 424/279

[56] References Cited

U.S. PATENT DOCUMENTS 3,990,880 11/1976 Mumford ............... 260/343.3 R
4,148,625 4/1979 Nagase ............... 260/343.3 R
4,179,444 12/1979 Roth ............... 260/343.3 R

OTHER PUBLICATIONS

Derwent Abstract 26410W/16 (75).

*Primary Examiner*—Jane T. Fan
*Attorney, Agent, or Firm*—Frederick H. Rabin; John P. Spitals

[57] ABSTRACT

The invention relates to cyclobutanedicarboxisoimides of the formula I

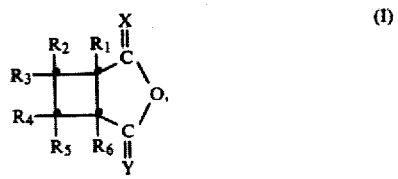

wherein one of X and Y is oxygen and the other is

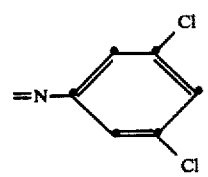

each of $R_1$ and $R_6$ independently is methyl or ethyl, each of $R_2$ and $R_3$ independently is hydrogen, fluorine or methyl, or $R_2$ is aceto hydrogen or methyl, while $R_3$ and $R_4$ together can also form an additional valency in the 4-membered cycloaliphatic ring. These compounds are suitable for controlling a variety of phytopathogenic fungi. They can be obtained by cyclizing the corresponding cyclobutanedicarboxylic acid monoamides in the temperature range from about $-20°$ to $+100°$ C., in the presence of dehydrating agents such as acetic anhydride or N,N'-dicyclohexylcarbodiimide.

9 Claims, No Drawings

CYCLOBUTANEDICARBOXISOIMIDES AND USE THEREOF AS FUNGICIDES

The present invention relates to novel cyclobutane dicarboxisoimides, to a process for their production, to fungicidal compositions containing them, and to a method of controlling fungi which comprises the use of these compounds.

From Japanese published patent specification 74/71 141 and from European published patent specification No. 0001395 it is known that 3,5-dihalophenylcyclobutane-carboximides which may be substituted at the cyclobutane ring have antimicrobicidal and also fungicidal properties and are suitable e.g. for controlling fungus diseases in rice.

The present invention provides cyclobutanedicarboxisoimides of the formula I

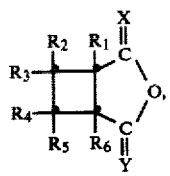

wherein one of X and Y is oxygen and the other is

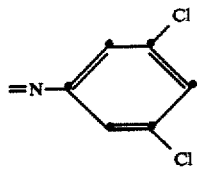

each of $R_1$ and $R_6$ independently is methyl or ethyl, each of $R_2$ and $R_3$ independently is hydrogen, fluorine or methyl, or $R_2$ is acetoxy or chlorine whilst $R_3$ is hydrogen, and wherein $R_4$ is hydrogen, methyl or chlorine, and $R_5$ is hydrogen or methyl, whilst $R_3$ and $R_4$ together can also form and additional valency in the 4-membered cycloaliphatic ring.

Preferred compounds of the formula I are those wherein each of $R_1$ and $R_6$ is methyl, each of $R_2$ and $R_3$ independently is hydrogen, fluorine or methyl, and each of $R_4$ and $R_5$ independently is hydrogen or methyl. Particularly preferred compounds of the formula I are those wherein each of $R_1$ and $R_6$ is methyl, each of $R_2$ and $R_3$ independently is hydrogen or fluorine, and each of $R_4$ and $R_5$ is hydrogen. The most preferred compound of the formula I is that wherein each of $R_1$ and $R_6$ is methyl and each of $R_2$, $R_3$, $R_4$ and $R_5$ is hydrogen.

The compounds of the formula I have excellent fungicidal properties and have, in particular, a pronounced action against Botrytis. The damage (grey mould) caused by Botrytis spp. (*B. cinerea, B alii*) on vines, strawberries, apples, onions and other varieties of fruit and vegetable, is a factor of considerable economic importance. The compounds of the formula I possess for practical purposes a very advantageous microbicidal structure for protecting cultivated plants without adversely affecting them by undesirable side-effects. Examples of cultivated plants within the scope of the present invention are: cereals, maize, rice, vegetables, sugarbeet, soya, ground nuts, fruit trees, especially drupes, ornamentals, vines, hops, cucumber plants (cucumber, marrows, melons), solanaceae such as potatoes, tobacco plants and tomatoes, and also banana, cocoa and natural rubber plants.

With the compounds of the formula I it is possible to inhibit or destroy the fungi which occur in plants or parts of plants (fruit, blossoms, leaves, stems, tubers, roots) in these and also related crops of useful plants, and also to protect from attack by such fungi the parts of plants which grow later. The compounds are effective against the phytopathogenic fungi which belong to the following classes: Ascomycetes (e.g. Erysiphaceae, Fusarium, Helminthosporium); Basidiomycetes, in particular rust fungi (e.g. Puccinia, Tilletia); fungi imperfecti (e.g. Moniliales, Cercospora, Sclerotinia, Botrytis and Piricularia); and against the Oomycetes such as Phytophthora or Plasmopara. The compounds of the formula I can also be used as seed dressing agents for protecting seeds (fruit, tubers, grains) and plant cuttings from fungus infections and from phytopathogenic fungi which occur in the soil.

The compounds of the formula I can be obtained e.g. by cyclising a cyclobutanedicarboxylic acid monoamide of the formula II

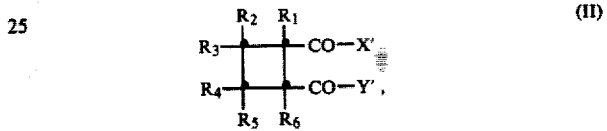

wherein one of X' and Y' is

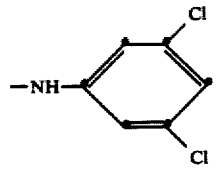

and the other is —OH, and $R_1$ to $R_6$ are as defined for formula I, in the temperature range from $-20°$ to $+100°$ C., preferably from $0°$ to $40°$ C., in the presence of a dehydrating agent and preferably in the presence of an inert organic solvent, to the isoimide of the formula I.

Isoimides are, in general, thermodynamically labile and rearrange readily to form the corresponding imides (see e.g. German Offenlegungsschrift No. 2 715 435). Surprisingly, the carboxamides of the formula II can be converted, under the indicated reaction conditions, into stable isoimides of the formula I.

Examples of suitable dehydrating agents are: anhydrides of aliphatic $C_2$–$C_5$ monocarboxylic acids which are unsubstituted or substituted by halogen atoms or $C_1$–$C_4$ alkyl groups, e.g. acetic, propionic, butyric and valeric anhydride, trichloro-, trifluoro-, trimethyl-, triethyl- and tri-n-butylacetic anhydride; carbodiimides such as N,N'-diisopropylcarbodiimide and N,N'-dicyclohexylcarbodiimide; and ketene. It is also possible to use mixtures of tertiary amines and the above specified anhydrides or mixtures of tertiary amines and unsubstituted or halogenated acetyl halides such as acetyl chloride, chloroacetyl chloride, dichloroacetyl chloride and trifluoroacetyl chloride. Examples of suitable tertiary amines are: N,N-dimethylaniline, N-methyl-N-ethylaniline, N-methyl- or N-ethyl morpholine, pyridine, quinuclidine or N,N'-dimethyl piperazine, and, in particular, trialkylamines containing 1 to 8 carbon atoms in each of the alkyl moieties, such as triethylamine, tri-n-butylamine, tri-(2-ethyl-n-hexyl)amine and tri-n-octylamine.

Preferred dehydrating agents are acetic anhydride, N,N'-dicyclohexylcarbodiimide, and ketene. Excess acetic anhydride can also be used as solvent.

Examples of suitable inert organic solvents for carrying out the cyclisation are unsubstituted or chlorinated aromatic hydrocarbons such as benzene, toluene, xylenes and chlorobenzene; chlorinated aliphatic hydrocarbons such as chloroform, methylene chloride and 1,2-dichloroethane; aliphatic and cycloaliphatic ketones such as acetone, methyl ethyl ketone and cyclohexanone; and dialkyl ethers containing 2 to 6 carbon atoms in each of the alkyl moieties, and cyclic ethers such as tetrahydrofurane and dioxane. It is most preferred to conduct the reaction in acetic anhydride or toluene.

When the reaction is complete, the isoimides of the formula I can be isolated in conventional manner, e.g. by distilling off the solvent and recrystallising the residue from a suitable solvent such as methanol, ethyl acetate or acetone.

The cyclobutanedicarboxylic acid monoamides of the formula II can be obtained e.g. by reacting a compound of the formula III

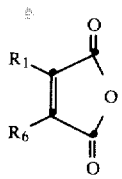

preferably in the presence of a photosensitiser, by the action of light, with a compound of the formula IV

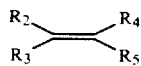

to give a compound of the formula V

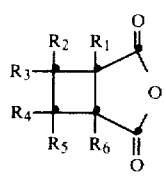

and reacting this latter with 3,5-dichloroaniline. In the formulae (III) to (V) above, $R_1$ to $R_6$ are as defined for formula I.

The above photochemical [2+2]-cycloaddition of a compound of the formula IV to a compound of the formula III is carried out with advantage in the presence of an inert organic solvent, in the temperature range from about $-80°$ to $+30°$ C., preferably from $-40°$ to $0°$ C.

Suitable inert organic solvents are those specified for the cyclisation. Preferred solvents are chlorinated aliphatic hydrocarbons, especially dichloromethane.

As photosensitisers it is possible to use compounds which are known per se, preferably those having an $E_T$ (triplet energy) of $\geq 230$ kj/moles [cf. Paul S. Engel and Bruce M. Monroe "Advance in Photochemistry", Vol. 8, 297–306, New York 1971]. Examples of such photosensitisers are benzophenone, acetophenone, biacetyl. In general, about 0.5 to 10% by weight of photosensitiser is used, based on the starting compound of the formula III.

The light source employed for the above photochemical reaction can be any light having wavelengths below 5000 Å. Examples of suitable light sources are mercury high-pressure lamps doped with metal atoms, xenon vapour lamps, mercury xenon lamps, mercury low or medium pressure lamps, halogen lamps or $D_2$ lamps.

The reaction of the anhydrides of the formula V with 3,5-dichloroaniline is carried out in a manner known per se, preferably in organic medium, in the temperature range from about 10° to 40° C.

The compounds of the formula I can be used by themselves or together with suitable carriers and/or adjuvants, in particular with surface-active agents. Suitable carriers and adjuvants can be solid or liquid and correspond to the substances normally used in the art of formulation, for example natural or regenerated mineral substances, solvents, dispersants, wetting agents, tackifiers, thickeners, binders or fertilisers. The compounds of the formula I can be used in admixture with other pesticidal compositions or compositions which promote plant growth.

The content of active ingredient in commercial formulations is between 0.1 and 90% by weight.

For application the compounds of the formula I may be processed to the following formulations (in which the percentages by weight refer to advantageous amounts of active ingredient):

Solid formulations: dusts, and tracking agents (up to 10% by weight), granules (coated granules, impregnated granules and homogeneous granules); pellets (1 to 80% by weight);

Liquid formulations:
(a) active ingredient concentrates which are dispersible in water: wettable powders, and pastes (25–90% by weight in commercial packs, 0.01 to 15% by weight in ready-for-use solutions); concentrated emulsions and solutions (10 to 50% by weight in commercial packs; 0.01% to 15% by weight in ready-for-use solutions);
(b) Solutions (0.1 to 20% by weight); aerosols.

PREPARATORY EXAMPLES

EXAMPLE 1

(a) In a low temperature exposure unit equipped with a 125 W mercury lamp in a cooled immersion bath, stirrer and gas inlet pipe, 15 g (0.12 mole) of dimethyl maleic anhydride and 1 g (0.0054 mole) of benzophenone are dissolved in 300 ml of dichloromethane, and the solution is cooled by means of an external cooling bath with a mixture of isopropanol and dry ice to $-60°$ to $-70°$ C. Ethylene gas is then introduced over 1 hour and the reaction mixture is subsequently irradiated at the above temperature for 12 hours while introducing a weak flow of ethylene. The solvent is then evaporated off and the crude product is recrystallised from dichloromethane/n-hexane, affording 10 g of 1,2-dimethylcyclobutane-1,2-dicarboxylic anhydride (54% of theory) in the form of white crystals with a melting point of 84°–86° C.

(b) 15.4 g (0.1 mole) of 1,2-dimethylcyclobutane-1,2-dicarboxylic anhydride are dissolved in 100 ml of toluene and to the solution are added 16.2 g (0.1 mole) of dichloroaniline. The reaction mixture is stirred for 16 hours at 25° C. and the precipitated colourless product is isolated, affording 27.8 g (88% of theory) of 1-(3,5- dichlorophenylcarbamoyl)-1,2-dimethylcyclobutane-1-carboxylic acid with a melting point of 164° C.

(c) 31.6 g of 1-(3,5-dichlorophenylcarbamoyl)-1,2-dimethylcyclobutane-1-carboxylic acid are stirred in 100 ml of acetic anhydride for 4 hours at 20° C. A clear solution forms after a short time. The acetic anhydride is distilled off in vacuo at 40° C. and the residue is recrystallised from methanol, affording 22 g of 1,2-dimethylcyclobutane-1,2-dicarboxylic acid (3,5-dichlorophenyl)isoimide with a melting point of 110°-111° C. Yield: 74% of theory. [Compound 1].

NMR spectrum (60 MHz, CHCl$_3$, δ in ppm): 1.35 (s, 3H, —CH$_3$); 1.45 (s, 3H, —CH$_3$); 2.0–2.7 (m, 4H, —CH$_2$CH$_2$—); 6.9–7.1 (m, 3H, aromat.).

IR spectrum (KBr): 1840 cm$^{-1}$ (s) and 1730 cm$^{-1}$ (vs).

Elemental analysis:
calculated C: 56.4%; H: 4.4%; Cl: 23.8%; found C: 56.5%; H: 4.4%; Cl: 24.0%.

EXAMPLE 2

15.8 g of 1-(3,5-dichlorophenylcarbamoyl)-1,2-dimethylcyclobutane-1-carboxylic acid are suspended in 100 ml of toluene. To this suspension is added a solution of 11 g of N,N'-dicyclohexylcarbodiimide in 100 ml of toluene. In the course of this addition the temperature rises to 30° C. After stirring for 3 hours at 20°-25° C., N,N'-dicyclohexylurea is filtered off and the filtrate is evaporated to dryness in vacuo at 40° C., affording 14.8 g (100% of theory) of 1,2-dimethyl-cyclobutane-1,2-dicarboxylic acid (3,5-dichlorophenyl)isoimide with a melting point of 110°-111° C. and the spectroscopic data of which are in accord with those of the compound obtained in Example 1.

The following compounds are also obtained in a manner similar to that described in either Example 1 or 2:

compound 2: 1,2,3- or 1,2,4-trimethylcyclobutane-1,2-dicarboxylic acid (3,5-dichlorophenyl)isoimide, m.p. 100°-102° C.;

compound 3: 1,3-dimethyl-3,3-(4,4)difluorocyclobutane-1,2-dicarboxylic acid (3,5-dichlorophenyl)isoimide, m.p. 68°-74° C.;

compound 4: 1,2-dimethylcyclobutene(3,4)-1,2-dicarboxylic acid(3,5-dichlorophenyl)isoimide, m.p. 108°-110° C.

Each of compounds 2 and 3 is a mixture of stereo- and regioisomers.

The compounds of the formula I can be processed e.g. to the following formulations:

EXAMPLE 3

Dusts: A ready-for-use 5% dust is formulated by grinding 5 parts of one of compounds 1 to 4 with 95 parts of talcum.

EXAMPLE 4

Granulate: The following constituents are used to formulate a 5% granulate:
5 parts of compound 1
0.25 part of epoxidised vegetable oil
0.25 part of cetyl polyglycol ether
3.50 parts of polyethylene glycol
91 parts of kaolin (particle size 0.3–0.8 mm).

The active ingredient is mixed with the epoxidised vegetable oil and the mixture is dissolved in 6 parts of acetone. Then polyethylene glycol and cetyl polyglycol ether are added. The resultant solution is sprayed on kaolin and the acetone is evaporated in vacuo. A microgranulate of this kind is advantageously used for controlling soil fungi.

EXAMPLE 5

Wettable powder: The following constituents are used to formulate (a) a 40%, (b) a 25% and (c) a 10% wettable powder:

(a) 40 parts of one of compounds 1 to 4,
5 parts of sodium lignosulfonate,
1 part of sodium dibutylnaphthalenesulfonate,
54 parts of silicic acid;

(b) 25 parts of one of compounds 1 to 4,
4.5 parts of calcium lignosulfonate,
1.9 parts of Champagne chalk/hydroxyethyl cellulose mixture (1:1),
1.5 parts of sodium dibutylnaphthalenesulfonate,
19.5 parts of silicic acid,
19.5 parts of Champagne chalk,
28.1 parts of kaolin;

(c) 10 parts of one of compounds 1 to 4,
3 parts of a mixture of the sodium salts of saturated fatty alcohol sulfates,
5 parts of naphthalenesulfonic acid/formaldehyde condensate,
82 parts of kaolin.

The active ingredients are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.

EXAMPLE 6

Emulsifiable concentrate: The following substances are used to formulate a 25% emulsifiable concentrate:
25 parts of one of compounds 1 to 4,
2.5 parts of epoxidised vegetable oil,
10 parts of an alkylarylsulfonate/fatty alcohol polyglycol ether mixture,
5 parts of dimethyl formamide,
57.5 parts of xylene.

By diluting such a concentrate with water it is possible to prepare emulsions of the desired concentration, which are especially suitable for leaf application.

BIOLOGICAL EXAMPLES

EXAMPLE 7

Action against Botrytis cinerea on beans (Vicia faba)

(a) Residual protective action

Bean plants about 10 cm in height are sprayed with a spray mixture (0.02% and 0.006% concentration) prepared from the active ingredient formulated as wettable powder. After 48 hours, the treated plants are infected with a conidia suspension of the fungus. The infected plants are incubated for 2 to 3 days at 95–100% relative humidity and 21° C., and evaluation of the fungus attack is then made. Compounds 1 to 4 in a concentration of 0.02% completely inhibited attack. Compounds 1, 2 and 4 also inhibited attack in a concentration of 0.006%.

(b) Action against Sclerotinia fructigena on apples

Artificially damaged apples are infected with *Sclerotinia fructigena* by pipetting a drop of mycelium suspension onto each injury site. After each drop has dried, the apples are sprayed with a wettable powder suspension of the active ingredient (0.02% concentration). The treated fruit is placed in plastic containers and stored for 14 days at 20°-22° C. Evaluation is made by counting the number of injury sites attacked by rot.

Compounds 1 to 4 completely inhibited attack.

(c) Action against Monilinia on cherry or peach blossoms: (moniliasis on drupes)

Individual fully flowered drupe branches are sprayed with a wettable powder (0.025% concentration) prepared from an emulsifiable concentrate. A few hours later the inflorescences are cut off, put into plastic dishes with the stem in wet sand, and inoculated with a spore suspension. The dishes are then loosely covered with transparent plastic sheeting and kept for 2 days at room temperature. The degree of attack is determined by counting the number of infected blossoms (40 blossoms are used per compound to be tested). Compounds 2 and 3 reduced attack to below 20%. Compounds 1 and 4 inhibited attack completely.

What is claimed is:

1. A compound of the formula I

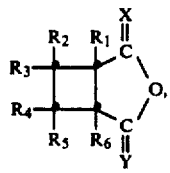

(I)

wherein one of X and Y is oxygen and the other is

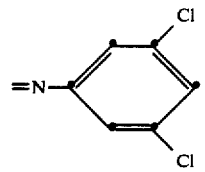

and wherein each of $R_1$ and $R_6$ independently is methyl or ethyl, each of $R_2$ and $R_3$ independently is hydrogen, fluorine or methyl or $R_2$ is acetoxy or chlorine whilst $R_3$ is hydrogen, and wherein $R_4$ is hydrogen, methyl or chlorine and $R_5$ is hydrogen or methyl, whilst $R_3$ and $R_4$ together can also form an additional valency in the four-membered cycloaliphatic ring.

2. A compound according to claim 1, wherein each of $R_1$ and $R_6$ is methyl, each of $R_2$ and $R_3$ is hydrogen, fluorine or methyl, and each of $R_4$ and $R_5$ is hydrogen or methyl.

3. A compound according to claim 2, wherein each of $R_2$ and $R_3$ is hydrogen or fluorine, and each of $R_4$ and $R_5$ is hydrogen.

4. The compound according to claim 3, wherein each of $R_2$ and $R_3$ is hydrogen.

5. A fungicidal composition which comprises, as active ingredient, an effective fungicidal amount of an isoimide according to claim 1, together with a suitable carrier therefor.

6. A method of controlling or preventing attack by phytopathogenic fungi, which method comprises applying to the locus to be protected an effective fungicidal amount of an isoimide according to claim 1.

7. A method of controlling or of preventing attack by phytopathogenic fungi, which method comprises applying to the locus to be protected an effective fungicidal amount of an isoimide according to claim 2.

8. A method of controlling or of preventing attack by phytopathogenic fungi, which comprises applying to the locus to be protected an effective fungicidal amount of an isoimide according to claim 3.

9. A method of controlling or of preventing attack by phytopathogenic fungi, which comprises applying to the locus to be protected an effective fungicidal amount of the compound according to claim 4.

* * * * *